United States Patent [19]
Murase et al.

[11] Patent Number: 5,777,330
[45] Date of Patent: Jul. 7, 1998

[54] METHOD OF RAPIDLY IDENTIFYING RESINS BY INFRARED SPECTROSCOPY AND SYSTEM THEREFOR

[75] Inventors: Atsushi Murase; Norio Sato, both of Nagoya; Takayuki Kato, Aichi-ken; Kazumasa Sumi, Nagoya, all of Japan

[73] Assignee: Nicolet Japan Corporation, Tokyo, Japan

[21] Appl. No.: 747,926

[22] Filed: Nov. 12, 1996

[30] Foreign Application Priority Data

Nov. 13, 1995 [JP] Japan .................... 7-319566

[51] Int. Cl.$^6$ .................... G01N 21/35; G01N 33/44
[52] U.S. Cl. .................... 250/339.13; 250/341.6
[58] Field of Search .................... 250/341.6, 339.12, 250/339.11, 339.13

[56] References Cited

U.S. PATENT DOCUMENTS

| | | | |
|---|---|---|---|
| 5,489,778 | 2/1996 | Burmester et al. | 250/341.6 |
| 5,512,752 | 4/1996 | Aikawa et al. | 250/339.12 |

FOREIGN PATENT DOCUMENTS

| | | |
|---|---|---|
| 6-3347 | 1/1994 | Japan . |
| 6-3348 | 1/1994 | Japan . |
| 6-3349 | 1/1994 | Japan . |
| 6-3350 | 1/1994 | Japan . |
| 6-3351 | 1/1994 | Japan . |
| 9200550 | 10/1993 | Netherlands . |

OTHER PUBLICATIONS

"Rapid Identification of Plastics," K. Vornberg et al. Kunstoffe Plast Europe, Published by Carl Hanser Verlag Munich vol. 84, Mar. 1994.

*Primary Examiner*—Edward J. Glick
*Attorney, Agent, or Firm*—Oblon, Spivak, McClelland, Maier & Neustadt, P.C.

[57] ABSTRACT

Infrared spectroscopy for rapidly identifying the kind of a plastic product on the spot. The surface of the plastic product is partially pyrolyzed in a quite short time to produce pyrolysis product gas. The gas is introduced into an infrared spectrophotometer to obtain an infrared absorption spectrum of the gas. The spectrum is collated with a pyrolysis infrared absorption spectrum of a standard sample. Thus, the plastic is identified. A heating probe comprising a heat radiation emitter mounted in the body of the probe, an opening formed in the body of the probe, an aperture formed in the body and located opposite to the opening, a reflecting mirror for directing the radiation into the opening, and a conduit for connecting thin ports in the probe with the spectrophotometer and with an external carrier gas source. The heat radiation emitter emits heat radiation for pyrolyzing the surface of the plastic product. The mirror is located near the aperture.

16 Claims, 2 Drawing Sheets

METHOD OF RAPIDLY IDENTIFYING RESINS BY INFRARED SPECTROSCOPY AND SYSTEM THEREFOR

BACKGROUND OF THE INVENTION

1. Field of the Invention

The present invention relates to a method of rapidly identifying the kinds of various plastics and, more particularly, to a method of rapidly identifying the kind of a plastic under examination on the spot, using a heating probe. The invention also relates to a system for carrying out this method.

2. Description of Related Art

In recent years, the necessity of recycling plastic wastes has increased worldwide because of environmental issues and problems with resources. Plastic recycling processes include: (i) material recycling involving remolding plastic waste without decomposing it; (ii) chemical recycling involving chemically decomposing plastic waste and recovering useful materials; and (iii) energy recycling involving burning plastic waste and recovering it in the form of thermal energy. Material recycling is adapted for large plastic automobile wastes such as bumpers and internal panels. In this case, it is necessary to rapidly identify the kinds of the materials.

In an attempt to meet this object, methods of identifying general plastic materials by making use of infrared spectroscopy and a method of identifying vinyl chloride resin by making use of an HCl detector have been proposed. Of the former methods, effective means proposed include: (1) rapid sorting of transparent plastic bottles, utilizing diffuse reflectance in the near-infrared, e.g., a system for automatically conveying, sorting, and separating waste plastic bottles; (2) a method of identifying colored plastics by making use of both diffuse reflectance in the near-infrared and optical fibers in combination, e.g., a machine for identifying reflection types and every kind of plastic; and (3) a method of identifying automobile plastic parts by making use of positive reflectance in the mid-infrared (K. Vornberger & B. Willenberg: "Rapid Identification of Plastics," Kunstoffe plast europe, vol. 84, March (1994)).

However, these methods have drawbacks. The method (1) above cannot be applied to colored plastics. The method (2) cannot be applied to black plastics. Since most automobile parts are black or otherwise colored, the methods (1) and (2) are unsuitable. The method (3) is adapted for colored plastics but it is necessary to convey plastic parts under examination to a measurement window in the apparatus because the optical path is fixed in principle. The method (2) is similar in this respect. However, in the case of a method using reflection, the identification is strongly affected by the state of the surface and by contamination. In order to obtain constant conditions, it is necessary to polish surfaces.

A method consisting of thermally decomposing plastics and identifying them from the decomposition products is available as a method which is unaffected by the surface state. This is generally known as pyrolysis infrared (Py-IR) spectroscopy or thermogravity infrared (TG-IR) spectroscopy. However, with these methods, it is necessary to cut out a sample and to place it in position within the instrument. Hence, these methods are not adapted for rapid identification which is necessary for recycling. Japanese Patent Laid-Open Nos. 3347-3351 disclose methods of identifying vinyl chloride resins. In these disclosed methods, the surfaces of the resins are decomposed by various heating probes. The resulting HCl gas is detected by an HCl detector. Thus, vinyl chloride resins are identified. Unfortunately, other kinds of plastics cannot be identified.

SUMMARY OF THE INVENTION

Accordingly, it is an object of the present invention to provide a method of identifying the kinds of plastic in a plurality of plastic samples rapidly, i.e., within 10 seconds, without moving the samples without the necessity of pretreatments (e.g., removable of contaminants such as oil and soot from the plastic samples) and without cutting out the samples. This identification has been impossible to achieve by any of the prior art techniques described above.

A first aspect of the present invention lies in a method of rapidly identifying a plastic object by infrared spectroscopy, the method comprising the steps of: pyrolyzing the surface partially in a short time to produce pyrolysis product gas; introducing the pyrolysis product gas into an infrared spectrophotometer; obtaining an infrared absorption spectrum of the introduced pyrolysis product gas by the spectrophotometer; and comparing the obtained spectrum with a pyrolysis infrared absorption spectrum of a standard sample, thus rapidly identifying the kind of the plastic.

The sample is partially heated. The produced gas is efficiently collected and carried into the body of the instrument. Therefore, the pyrolysis product gas can be measured without cutting out the samples. It is necessary that the samples be heated up to their pyrolysis temperatures in a short time. If they are gradually heated, even plastics of the same component give rise to gases of varying compositions. Consequently, it is impossible to rapidly identify them precisely. In order to obtain stable pyrolysis product gas components, it is necessary to stabilize the heating temperature at which the sample is fully decomposed.

It is necessary to rapidly draw the gas into the infrared spectrophotometer without changing the gaseous state. This will permit rapid, stable measurements. The gases produced by pyrolysis consist of monomers and oligomers produced by the decomposition or thermal degradation of the plastics under examination. Hence, the gases reflect the features of the chemical structures of the plastics. Accordingly, the samples can be identified by obtaining spectra of the gases by the infrared spectrophotometer and comparing the spectra with a spectrum of a standard sample previously obtained under the same heating conditions. In this case, it is not necessary to pretreat the samples as it would be with ordinary infrared spectroscopy. As a result, the rate at which plastics are identified can be increased almost up to the limit imposed by the measuring speed of the infrared spectrophotometer. Furthermore, the gases produced by decomposition of the samples are investigated and so the samples might be distinguished from each other more clearly where spectra of polymerized plastics are created, e.g., nylon-6 and nylon-6, 6.

In one feature of the invention, if the resins are colored, they are heated preferably for 1 to 5 seconds. If they are heated for a longer time, then the measuring time is prolonged. In addition, a countermeasure against rise of the temperature of the body of the probe is necessary. If the heating time is too short, resins are not sufficiently thermally decomposed.

In another feature of the invention, the heating temperature is preferably between 500° and 1000° C. If a temperature lower than this range is used, some plastics may not be pyrolyzed fully. Furthermore, if the temperature is lower, the pyrolysis rate is smaller, and it is time-consuming to obtain pyrolysis product gases. This makes it difficult to perform rapid measurements. On the other hand, if the temperature is higher than the above-described range, the decomposition may progress too rapidly. In this case, it may be difficult to identify the plastics. For measurements of ordinary resins, the preferred pyrolysis temperature is 600°–800° C.

A heating probe constructed as described now can be used for generation of the pyrolysis product gases described above. The heating probe comprises an opening formed in a hollow body and acting to collect a pyrolysis product gas produced from the surface of the resin subjected to pyrolysis, a heat radiation-emitting means mounted in the body and acting to emit heat radiation for pyrolyzing the surface of the resin, a reflecting mirror for focusing the radiation from the heat radiation-emitting means into the opening, thin ports formed in the body and acting to guide gas collected in the body into an infrared spectrophotometer, and a conduit for connecting one of said thin ports with the infrared spectrophotometer and another of said thin ports with an external carrier gas source. The body is provided with an aperture which has a constant diameter that is the same as that of the opening, or the diameter increases from the same diameter outwardly. The aperture is located on the opposite side of the opening. The reflecting mirror is mounted near the aperture.

Preferably, the opening in the probe is smaller than a specimen under investigation. The size of the opening permits pyrolysis product gas produced from the sample to be collected sufficiently. The size of the aperture located on the opposite side of the opening depends on the size of a heat-generating body or on the size of the reflecting mirror. If the focal distance of the reflecting mirror is too large, then the probe is too large, and the produced gas stays for a prolonged time, i.e., the residence time is increased. This increases the measuring time. On the other hand, if the focal distance is too small, a sufficient space cannot be secured between the opening and the reflecting mirror. Consequently, a lamp or the like cannot be well received. The distance between the heat-generating body and the sample and the amount of radiation may be so set that a sufficient amount of gas is obtained for measurements. The focal distance of the reflecting mirror, the position of the heat-generating body, and the length of the probe may be determined so as to satisfy these conditions. If the aforementioned distance is small, then a sufficient amount of gas is not derived. If the distance is large, the emitting surface becomes nonuniform in temperature. Hence, stable pyrolysis conditions are not obtained.

The body of the probe may assume any desired form as long as it easily receives energy from the heat source and collects the produced pyrolysis product gas. In order to introduce the pyrolysis product gas collected in the body into the infrared spectrophotometer, it is necessary to form a pair of thin ports.

Preferably, the above-described conduit is flexible and capable of being heated. In this case, the heating probe for the rapid identification of resins can be operated at will according to the object to be measured at a location remote from the infrared spectrophotometer.

Preferably, the probe further comprises a switch for starting a measurement and packing for collecting the gas mounted in the opening in the heating probe. This increases the efficiency with which the gas is collected. Consequently, the measurement can be repeated at short intervals of time.

The present invention also provides a system comprising: a heating probe having a pair of thin ports; an infrared spectrophotometer for obtaining infrared absorption spectra of pyrolysis product gases which are collected by the heating probe and have been carried out of the probe; an external carrier gas source for supplying a carrier gas for carrying the pyrolysis product gas collected inside the body of the probe into the infrared spectrophotometer through a conveyance path when measurements are made by the spectrophotometer and for purging the conveyance path after or before a measurement; a conduit for connecting one of said thin ports in the heating probe with the infrared spectrophotometer and another of said thin ports with the carrier gas source; a solenoid valve mounted between the infrared spectrophotometer and the conduit; another solenoid valve mounted between the external carrier gas source and the conduit, said solenoid valves permitting modifications of the conveyance path; and a computer for controlling the solenoid valves and recording and analyzing spectral data from the infrared spectrophotometer. Thus, the system rapidly identifies resins by infrared spectroscopy. The heating probe comprises an opening formed in the body of the probe, an aperture formed in the body of the probe and located on the opposite side of the opening, a heat radiation-emitting means mounted in the body and acting to emit heat radiation for partially pyrolyzing the surface of a resinous object, a reflecting mirror for focusing the radiation from the heat radiation-emitting means into the opening, and the aforementioned thin ports for carrying pyrolysis product gas collected inside the body out of the body. The aperture has a constant diameter which is the same as the diameter of the opening, or the aperture increases in diameter from the same diameter outwardly. The reflecting mirror is located near the aperture.

The surface of the plastic object under investigation is pyrolyzed in a short time by the heating probe. This gives rise to pyrolysis product gas. The generated gas is carried into a gas cell mounted in the infrared spectrophotometer by an external gas through the conduit heated by the probe. Then, infrared spectra are obtained. The measurement can be automated by modifying the gas flow line by the solenoid valves controlled by a sequencer or the computer. This permits measurements to be performed rapidly, easily, and precisely.

In one feature of the invention, the aforementioned heat radiation-emitting means pyrolyzes the resin for 1 to 5 seconds.

In another feature of the invention, the heat radiation-emitting means pyrolyzes the resin at a temperature of 500° to 1000° C.

In a further feature of the invention, the heat radiation-emitting means pyrolyzes the resin at a temperature of 600° to 800° C.

In a still other feature of the invention, the conduit has flexibility and is capable of being heated.

In a yet further feature of the invention, the probe further comprises a switch for starting a measurement and packing for collecting the pyrolysis product gas mounted in the opening.

Other objects and features of the invention will appear in the course of the description thereof, which follows.

DETAILED DESCRIPTION OF THE PREFERRED EMBODIMENTS

Figure 1:
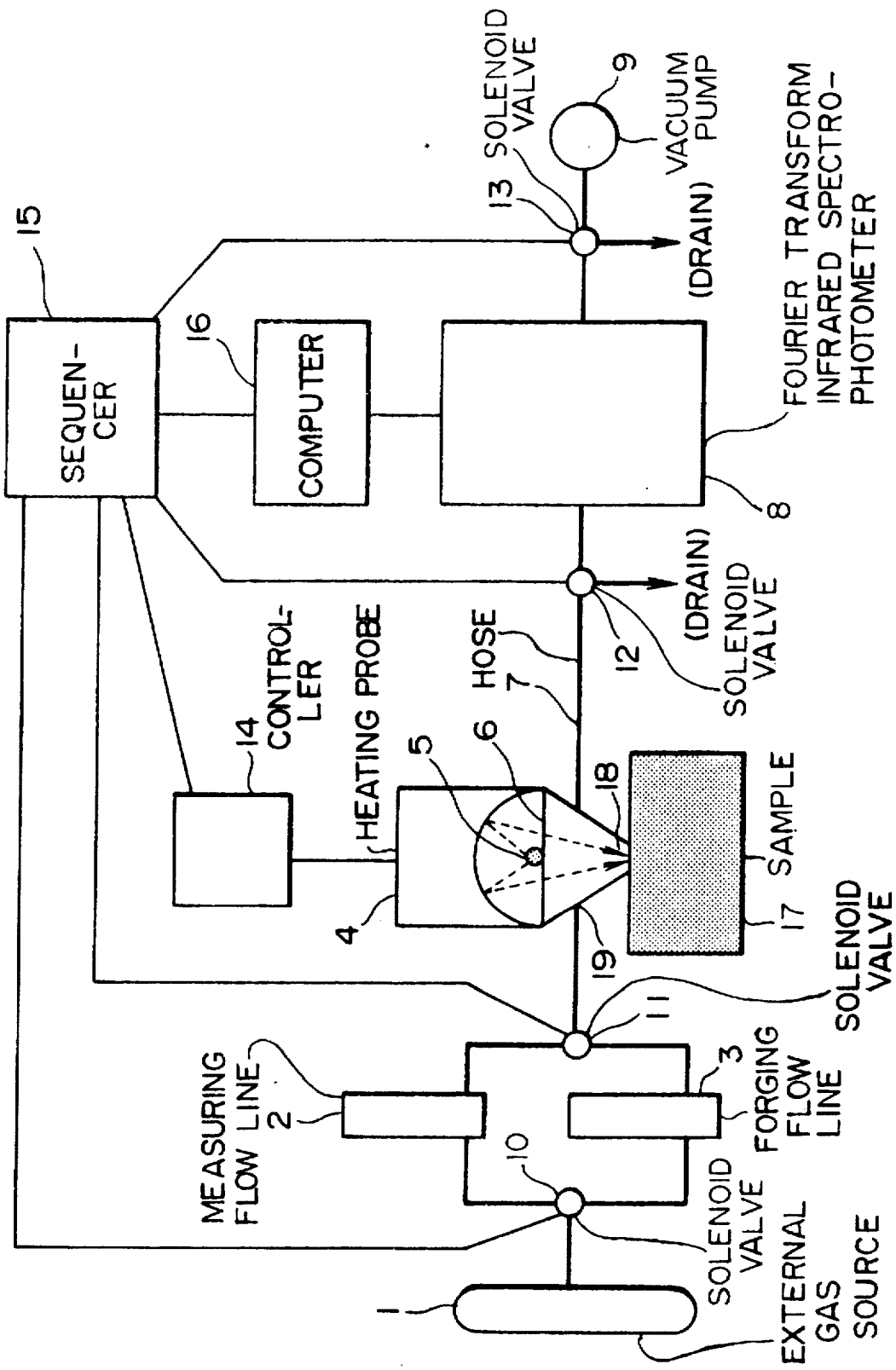
FIG. 1 is a block diagram of a system for carrying out a method according to the present invention.

In order to obtain pyrolysis product gas components stably from a sample, it is necessary to stabilize the heating temperature at which the sample is completely decomposed. A halogen lamp, near-infrared lamp, infrared laser, or the like can be appropriately used as a heat source for the above-described purpose.

It is necessary that the produced gas be rapidly drawn into an infrared (IR) spectrophotometer while the gas is retained in a gaseous state. The method of drawing the gas into the IR instrument can consist of (1) pumping the produced gas into the IR instrument by a vacuum pump, (2) evacuating the inside of the measurement cell within the IR instrument by a rotary pump or the like and drawing the produced gas into the cell, and (3) using these methods in combination. In order to rapidly draw the pyrolysis product gas into the IR instrument efficiently by any one of these methods, it is necessary to operate the valves appropriately.

The size of the opening in the heating probe is so set that partial pyrolysis of the sample can be sufficiently accomplished and that the pyrolysis product gas produced from the sample can be collected sufficiently. Normally, a size considerably smaller than the sample will suffice. Preferably, the area of the opening is 1 to 5 $cm^2$. If rubber packing such as an O-ring is mounted in the opening, the probe comes into contact with the sample sufficiently intimately, and the pyrolysis product gas can be collected in full. The size of the aperture depends on the size of the heat-generating body and on the size of the reflecting mirror. Preferably, the area of the aperture is 20 to 50 $cm^2$. The focal distance of the reflecting mirror is preferably 30 to 100 mm. If the focal distance is in excess of this range, the probe is too large, thus increasing the residence time of the produced gas. This prolongs the measuring time. On the other hand, if the focal distance is too small, a sufficient space cannot be secured between the opening and the reflecting mirror. As a consequence, the heat-generating body cannot be well received. The distance between the heat-generating body and the sample under investigation and the amount of radiation may be so set that a sufficient amount of gas is obtained for measurements. The focal distance of the reflecting mirror, the position of the heat-generating body, and the length of the probe may be determined so as to satisfy these conditions. The distance between the heat-generating body and the sample is preferably 1 to 5 mm, although it may be affected by the output from the heat-generating body. If the distance is small, then a sufficient amount of gas is not derived. If the distance is large, the emitting surface becomes nonuniform in temperature. Hence, neither stable pyrolysis conditions nor stable measuring conditions are obtained.

The body of the probe may assume any desired form as long as it easily receives energy from the heat source and collects the pyrolysis product gas. Preferably, the shape is cylindrical, conical, prismatic, or pyramidal form. Any desired substance may be used as the material of the body of the probe as long as it is heatproof, chemical resistant, and can withstand loads of about 2 kg__f. For example, the body of the probe is preferably made of stainless steel.

Walls for partitioning the interior of the probe according to the flow of the gas may be appropriately mounted. Where the walls block radiation from the reflecting mirror, it is necessary that the material of the walls be transparent. For instance, the material may be quartz.

The conduit connected with the heating probe is preferably capable of being heated up to about 200° C. and is flexible. If no heating is done, a part of the pyrolysis product gas condenses within the conduit. This will produce noise when identification is done. As an example, the conduit is made of a Teflon tube around which a heater is wound. The temperature may be controlled by a slide rheostat or the like.

The sample is pyrolyzed by the heating probe. The produced gas is collected and carried into the gas cell inside the IR instrument from the probe through the heated conduit by an external carrier gas. Then, IR spectra are obtained. At this time, the external carrier gas may be an inert gas such as nitrogen gas.

EXAMPLE 1

A system according to the present invention is shown in FIG. 1. The system has a heating probe 4 consisting of a near-infrared spot heater 5 equipped with a reflecting mirror having a diameter of 45 mm and a focal distance of 39 mm. The body of the probe 4, connected to a sequencer 15 by way of a controller 14, as shown in FIG. 1, is made of stainless steel and assumes a conical form. The body is provided with an opening 18 having a diameter of 20 mm. The spot heater heats an area of the surface of the sample having a diameter of approximately 5 mm. The probe 4 is formed with a pair of thin ports 19 to permit gas to go into and out of the probe. In order to reduce the volume inside the probe and to prevent the reflecting mirror from getting contaminated, a transparent quartz plate 6 is placed under the spot heater 5 and above the opening 18 and thin ports 19. A hot hose 7 comprises a Teflon tube around which a heater is coiled. The hose 7 can be heated up to about 200° C. In this example, the temperature is controlled to 150° C. A Fourier transform (FT) infrared (IR) spectrophotometer 8 contains a gas cell which is heated to 200° C. in use.

An automobile part made from plastic was recovered from the market. This plastic part was identified by this system in the manner described now. This part was circular and had a diameter of about 40 cm. The part was curved throughout its whole surface. In addition, complex shapes are given to some portions of the plastic part for reinforcing and aesthetical purposes. The portion of the plastic part which is completely flat is very small. The procedure is given below.

(1) The heating probe 4 was brought into intimate contact with a sample 17 under investigation. At the same time, solenoid valves 10 and 11 were so operated that a purging flow line 3 was made usable. The inside of the probe was purged by supplying $N_2$ gas from an external gas source 1 through the purging flow line 3 at a flow rate of 5 liters/min. Concurrently, a solenoid valve 12 was switched to a state in which the probe was connected to the drain line. Another solenoid valve 13 was switched to a state in which a vacuum pump 9 was connected with the Fourier transform infrared spectrophotometer 8. In this way, the inside of the sample cell in the FT IR instrument 8 was placed in a subatmospheric condition.

(2) After purging the inside of the probe for 2 seconds, the solenoid valves 10 and 11 were connected with a measuring flow line 2 through which $N_2$ gas from an external gas source 1 flows at a flow rate of 0.5 liter/min. The solenoid valve 12 was so operated that the probe was connected with the FT IR instrument. At the same time, the sample surface was heated for 2 seconds by the spot heater to pyrolyze the surface. The produced gas was introduced into the cell in about 2 seconds by the reduced pressure inside the gas cell contained in the FT IR instrument and by the pressure of the nitrogen.

(3) An IR spectrum was obtained from the gas introduced into the cell immediately after the heating. The results were collated by a computer 16 with a reference spectrum previously obtained, whereby the sample was identified. The result was displayed on a CRT. It required about 2 seconds for the measurement.

When it was about 5 seconds since the heating was started, the measurement was completed. Then, the solenoid valves 10 and 11 were switched to the side of the purging flow line. The solenoid valve 13 was switched to the drain line. Thus, the inside of the probe and the inside of the cell contained in the FT IR instrument were purged for 2 seconds.

The operations for activating the valves in the manner described above are carried out under the control of a sequencer 15. In this way, a series of operations for identifying the sample is completed within 10 seconds.

Figure 2:
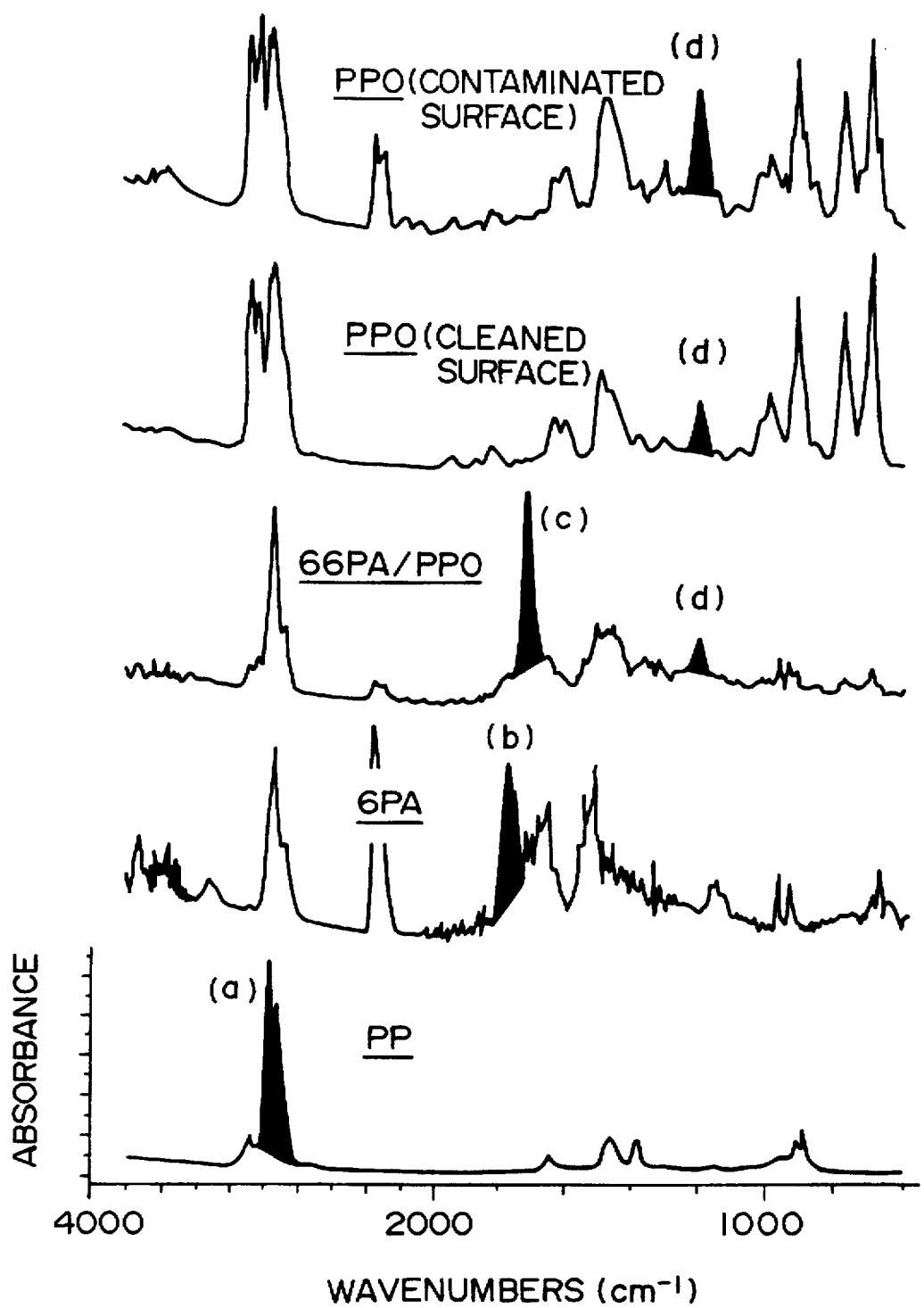
FIG. 2 is a graph illustrating infrared absorption spectra obtained by typical methods according to the invention.

Examples of the results are shown in FIG. 2, which depicts infrared spectra of four kinds of resins. The spectra were obtained after 2 seconds since they were heated. In FIG. 2, peak (a) indicates $CH_2$ and $CH_3$ of polypropylene resin. Peak (b) indicates ε-caprolactam which is a monomer of nylon-6. Peak (c) indicates cyclopentane that is a pyrolysis product of nylon-6,6. Peak (d) indicates the aromatic ether structure of polyphenylene oxide. Using these peaks as indications, four kinds of resins, i.e., polypropylene, nylon-6, nylon-6,6, and polyphenylene oxide, could be clearly identified, as well as their compounds.

Especially, the difference between nylon-6 and nylon-6,6 appeared much more clearly than on normal infrared spectra. Where a surface heavily contaminated with soot or the like was measured, the amounts of carbon dioxide, methane, and other components increased, but they did not obscure the peaks characteristic to the resins. We have confirmed that they were not an obstacle to identification.

Similarly, 50 samples consisting of four kinds of resins were measured at random. We confirmed that they could be identified with complete accuracy, irrespective of whether they were contaminated and irrespective of the degrees of roughness of the surfaces.

EXAMPLE 2

The recovered plastic products sorted in Example 1 were recycled by the procedure described below.

(1) Coatings were peeled off the sorted products of polypropylene, nylon-6, nylon-6,6, and polyphenylene oxide. The remaining plastic products were cut into pieces by a chopper.

(2) The four types of plastics were introduced into different melting furnaces and melted. Then, they were cooled. As a result, recycled products of the plastics were obtained. Where plastics of thermosetting resins were sorted, it was difficult to melt and recycle them. Therefore, they were recycled, using chemicals. For example, in the case of urea resin, the recovered products were made to plasticize by hydrolysis before being recycled.

(3) The recycled polypropylene had mechanical characteristics comparable to those of virgin polypropylene resins and so the recycled resins were reused in the same way as the material of the virgin resins.

(4) Other recycled plastics showed mechanical characteristics poorer than those of virgin plastics. Therefore, they were reused as materials of other kinds of products.

(5) Depending on the applications, these recycled plastics could be reused by mixing them with different kinds of plastics or mixing them into virgin plastics.

EXAMPLE 3

With respect to recovered plastic products having coatings, the heating probe was pressed against uncoated portions of the products, thus decomposing and vaporizing the underlying plastics. In this way, pyrolysis product gases were obtained. Depending on the recovered products, it was effective in obtaining the gases from the rear surfaces of the products.

In the present example, two thermal shots were performed to vaporize the coatings. Then, pyrolysis product gases were obtained from the exposed, underlying plastics. In this manner, recovered coated plastic products were sorted.

COMPARATIVE EXAMPLE

The same recovered plastic products as used in Example 1 were identified by pyrolysis infrared (Py-IR) spectroscopy, which is a conventional technology. In this technology, tar is detected by attenuated total reflectance (ATR) spectroscopy. It took about 10 minutes, including the time required for preparation of a sample, to obtain it. This time is 60 times as long as the time required in the novel method. Furthermore, the difference between nylon-6 and nylon-6,6 was quite unclear in the pyrolysis infrared (Py-IR) spectroscopy, although the difference was clear in the novel method.

The quality of information obtained by thermogravity infrared (TG-IR) spectroscopy which is another pyrolysis infrared spectroscopy technology was quite similar to that of the information obtained by the novel method. The above-described kinds of nylon could be clearly identified. However, the measuring time including the time required for preparation of the sample was about 30 minutes, which is about 200 times as long as the time required in the novel method. Furthermore, the structure of the instrument makes it impossible to measure large samples directly. Hence, it is necessary to section the sample.

It was attempted to identify the same recovered products similarly by the infrared reflection technology which is currently regarded as most suitable for identification of automobile parts. Good spectra were obtained from clean surfaces, and they could be identified. However, no spectra were obtained from contaminated surfaces or from rough surfaces, and so polishing was necessary. The identification time including the time required for the polishing was about 30 seconds. In this way, more labor and a longer time were necessary than in the novel method. In addition, the above-described kinds of nylon could not be clearly identified.

What is claimed is:

1. A method of rapidly identifying a resin by infrared spectroscopy, said method comprising the steps of:
   pyrolyzing a surface of the resin partially in a short time to produce a pyrolysis product gas;
   introducing said pyrolysis product gas into an infrared spectrophotometer;
   obtaining an infrared absorption spectrum of said pyrolysis product gas by said infrared spectrophotometer; and
   collating said obtained spectrum with a pyrolysis infrared absorption spectrum of a standard sample, whereby identifying said resin rapidly.

2. A method of rapidly identifying a resin by infrared spectroscopy as set forth in claim 1, wherein said resin is colored, and wherein said surface of the resin is pyrolyzed for 1 to 5 seconds.

3. A method of rapidly identifying a resin by infrared spectroscopy as set forth in claim 2, using a heating probe comprising:
   a hollow body;
   an opening formed in said hollow body and acting to collect said pyrolysis product gas produced from the surface of the resin, said opening having a given diameter;

an aperture formed in said body and located opposite to said opening, said aperture having a diameter which is equal to or greater than said given diameter of said opening;

a heat radiation-emitting means mounted in the body, said heat radiation-emitting means acting to emit heat radiation for pyrolyzing the surface of the resin;

a reflecting mirror for focusing the radiation from the heat radiation-emitting means into said opening, said mirror being located near said aperture;

a pair of thin ports formed in the body and acting to guide the gas collected in the body into said infrared spectrophotometer; and a conduit for connecting one of said thin ports with said infrared spectrophotometer and another of said thin ports with an external carrier gas source.

4. A method of rapidly identifying a resin by infrared spectroscopy as set forth in claim 1, wherein said surface of the resin is pyrolyzed at a temperature of 500° to 1000° C.

5. A method of rapidly identifying a resin by infrared spectroscopy as set forth in claim 4, using a heating probe comprising:

a hollow body;

an opening formed in said hollow body and acting to collect said pyrolysis product gas produced from the surface of the resin, said opening having a given diameter;

an aperture formed in said body and located opposite to said opening, said aperture having a diameter which is equal to or greater than said given diameter of said opening;

a heat radiation-emitting means mounted in the body, said heat radiation-emitting means acting to emit heat radiation for pyrolyzing the surface of the resin;

a reflecting mirror for focusing the radiation from the heat radiation-emitting means into said opening, said mirror being located near said aperture;

a pair of thin ports formed in the body and acting to guide the gas collected in the body into said infrared spectrophotometer; and a conduit for connecting one of said thin ports with said infrared spectrophotometer and another of said thin ports with an external carrier gas source.

6. A method of rapidly identifying a resin by infrared spectroscopy as set forth in claim 1, wherein said surface of the resin is pyrolyzed at a temperature of 600° to 800° C.

7. A method of rapidly identifying a resin by infrared spectroscopy as set forth in claim 6, using a heating probe comprising:

a hollow body;

an opening formed in said hollow body and acting to collect said pyrolysis product gas produced from the surface of the resin, said opening having a given diameter;

an aperture formed in said body and located opposite to said opening, said aperture having a diameter which is equal to or greater than said given diameter of said opening;

a heat radiation-emitting means mounted in the body, said heat radiation-emitting means acting to emit heat radiation for pyrolyzing the surface of the resin;

a reflecting mirror for focusing the radiation from the heat radiation-emitting means into said opening, said mirror being located near said aperture;

a pair of thin ports formed in the body and acting to guide the gas collected in the body into said infrared spectrophotometer; and a conduit for connecting one of said thin ports with said infrared spectrophotometer and another of said ports with an external carrier gas source.

8. The heating probe of claim 7, wherein said conduit is flexible and is capable of being heated.

9. The heating probe of claim 8, further comprising a switch for starting a measurement and packing for collecting said pyrolysis produce gas mounted in said opening.

10. A method of rapidly identifying a resin by infrared spectroscopy as set forth in claim 1, using a heating probe comprising:

a hollow body;

an opening formed in said hollow body and acting to collect said pyrolysis product gas produced from the surface of the resin, said opening having a given diameter;

an aperture formed in said body and located opposite to said opening, said aperture having a diameter which is equal to or greater than said given diameter of said opening;

a heat radiation-emitting means mounted in the body, said heat radiation-emitting means acting to emit heat radiation for pyrolyzing the surface of the resin;

a reflecting mirror for focusing the radiation from the heat radiation-emitting means into said opening, said mirror being located near said aperture;

a pair of thin ports formed in the body and acting to guide the gas collected in the body into said infrared spectrophotometer; and a conduit for connecting one of said thin ports with said infrared spectrophotometer and another of said thin ports with an external carrier gas source.

11. A system for rapidly identifying a resin by infrared spectroscopy, said system comprising:

a heating probe having a hollow body, an opening formed in the body of the probe and having a given diameter, an aperture formed in the body of the probe and located on the opposite side of the opening, said aperture having a diameter which is equal to or greater than said given diameter of said opening, a heat radiation-emitting means mounted in the body and acting to emit heat radiation for partially pyrolyzing the surface of the resin, a reflecting mirror for focusing the radiation from the heat radiation-emitting means into said opening, said reflecting mirror being located near said aperture, and a pair of thin ports for carrying pyrolysis product gas collected inside the body out of the body through a conveyance path;

an infrared spectrophotometer for obtaining an infrared absorption spectrum of said pyrolysis product gas carried out of said heating probe;

an external carrier gas source for supplying a carrier gas which carries said pyrolysis product gas collected inside the body of said heating probe into said infrared spectrophotometer when said pyrolysis product gas is analyzed by said infrared spectrophotometer and for purging said conveyance path before or after a measurement;

a conduit for connecting one of said thin ports in said heating probe with said infrared spectrophotometer and another of said thin ports with said external carrier gas source;

a solenoid valve mounted between said infrared spectrophotometer and said conduit for modifying said conveyance path;

another solenoid valve mounted between said external carrier gas source and said conduit for modifying said conveyance path; and a sequencer for controlling said solenoid valves;

and a computer for recording and analyzing spectral data obtained by said infrared spectrophotometer.

12. The system of claim 11, wherein said heat radiation-emitting means pyrolyzes said resin for 1 to 5 seconds.

13. The system of claim 11, wherein said heat radiation-emitting means pyrolyzes said resin at a temperature of 500° to 1000° C.

14. The system of claim 13, wherein said heat radiation-emitting means pyrolyzes said resin at a temperature of 600° to 800° C.

15. The system of claim 11, wherein said conduit is flexible and is capable of being heated.

16. The system of claim 11, further comprising a switch for starting a measurement and packing for collecting said pyrolysis product gas mounted in said opening.

* * * * *